US010117660B2

(12) United States Patent
Cook et al.

(10) Patent No.: US 10,117,660 B2
(45) Date of Patent: Nov. 6, 2018

(54) IMPACT DRILL LITHOTRIPTER

(71) Applicant: Gyrus ACMI, Inc., Southborough, MA (US)

(72) Inventors: Chris A. Cook, New York, NY (US); Kurt G. Shelton, Woburn, MA (US); Tie Hu, Marlborough, MA (US)

(73) Assignee: GYRUS ACMI, INC., Southborough, MA (US)

( * ) Notice: Subject to any disclaimer, the term of this patent is extended or adjusted under 35 U.S.C. 154(b) by 144 days.

(21) Appl. No.: 14/643,674

(22) Filed: Mar. 10, 2015

(65) Prior Publication Data

US 2016/0038165 A1   Feb. 11, 2016

Related U.S. Application Data

(60) Provisional application No. 62/034,876, filed on Aug. 8, 2014.

(51) Int. Cl.
*A61B 17/22* (2006.01)
*A61B 17/00* (2006.01)
*A61B 17/32* (2006.01)

(52) U.S. Cl.
CPC .. *A61B 17/22012* (2013.01); *A61B 17/22004* (2013.01); *A61B 17/320068* (2013.01); *A61B 2017/00017* (2013.01); *A61B 2017/0023* (2013.01); *A61B 2017/22015* (2013.01); *A61B 2017/22025* (2013.01); *A61B 2017/22079* (2013.01); *A61B 2560/0214* (2013.01)

(58) Field of Classification Search
None
See application file for complete search history.

(56) References Cited

U.S. PATENT DOCUMENTS

| | | | |
|---|---|---|---|
| 1,657,765 A | | 1/1928 | Pasque |
| 5,160,336 A | | 11/1992 | Favre |
| 5,176,688 A | | 1/1993 | Narayan et al. |
| 5,722,980 A | | 3/1998 | Schulz |
| 5,925,055 A | | 7/1999 | Adrian |
| 2006/0155210 A1 | | 7/2006 | Beckman et al. |
| 2011/0245736 A1 | | 10/2011 | Foehrenbach |
| 2011/0295270 A1 | * | 12/2011 | Giordano ......... A61B 17/00234 606/130 |

FOREIGN PATENT DOCUMENTS

| | | |
|---|---|---|
| JP | 07-308323 A | 11/1995 |
| WO | 2008144274 A2 | 11/2008 |

* cited by examiner

*Primary Examiner* — Shaun L David (57) ABSTRACT

A lithotripter includes a motor operable to produce a rotational motion, a first cam with a first set of teeth, and a second cam with a second set of teeth configured to selectively engage with the first set of teeth. The first cam is coupled to the motor so that the rotational motion produced by the motor produces rotational motion of the first cam, and the selective engagement between the first set of teeth and the second set of teeth converts the rotational motion of the first cam to a linear waveform that is transmitted through the second cam. The motor, the first cam, and the second cam are disposed in a driver housing, and a wave guide shaft is coupled to the second cam. The wave guide shaft transmits the linear waveform to at least one urinary tract stone to break up the at least one urinary tract stone into fragments.

16 Claims, 6 Drawing Sheets

IMPACT DRILL LITHOTRIPTER

RELATED APPLICATION

This application claims the benefit of U.S. Provisional Patent Application No. 62/034,876, filed on Aug. 8, 2014, the entire contents of which are incorporated herein by reference.

FIELD

The present disclosure relates to a medical device. More specifically, the present disclosure relates to a lithotripter for fragmenting stones in a patient's body.

BACKGROUND

The statements in this section merely provide background information related to the present disclosure and may or may not constitute prior art.

Lithotripsy is a common method for fragmenting stones, or calculi, in the urinary tract, kidneys, and/or bladder. Most lithotripsy devices use ultrasound, laser, or pneumatic energy sources to fragment such stones. Typically, the lithotripter includes a shaft connected to an electrically controlled driver or a pneumatic actuator. The shaft is inserted into the patient's anatomy to a location near the stone, and a waveform is sent through the shaft to impact the stone with the shaft to create a jackhammer or drilling effect on the stone, thus fragmenting the stone into smaller elements that are easier to remove. The stone fragments are then removed by irrigation and/or baskets.

Among the literature that can pertain to this technology include the following patent documents and published patent applications: US 2011/0245736; US 2006/0155210; U.S. Pat. No. 1,657,765; U.S. Pat. No. 5,160,336, and WO2008/144274, all incorporated by reference for all purposes.

Current lithotripsy devices may be expensive, complicated, and/or less effective at fragmenting stones than desired. For example, certain lithotripsy devices employ compressed gas that delivers a single pulse of energy to fragment urinary calculi with each activation. Fragments are then removed with a different device. Further, a new cartridge of compressed gas is required for each procedure, and the various components associated with these types of devices are sterilized and disinfected between procedures. In other lithotripsy systems, the driver that delivers the waveform to the stone and the control module that operates the driver are separate components. Some parts of the driver may be disposable, but other parts are cleaned and disinfected before each procedure.

Accordingly, there exists a need for more effective, simpler, and/or less expensive lithotripsy devices.

SUMMARY

The present invention provides an improved lithotripter that is disposable, or partially disposable, and does not require an additional external control system to operate the lithotripter.

Accordingly, pursuant to one aspect of the invention, which may be combined with or separate from other aspects of the invention, there is contemplated a lithotripter for fragmenting urinary tract stones. The lithotripter includes a motor operable to produce a rotational motion, a first cam with a first set of teeth, and a second cam with a second set of teeth configured to selectively engage with the first set of teeth. The first cam is coupled to the motor so that the rotational motion produced by the motor produces rotational motion of the first cam, and the selective engagement between the first set of teeth and the second set of teeth may convert the rotational motion of the first cam to a linear waveform that is transmitted through the second cam. Selective engagement of the first set of teeth with the second set of teeth may convert the rotational motion of the first cam to a linear waveform with some rotation that is transmitted through the second cam. The specific proportion of the conversion from rotational motion to linear motion may be controlled by the geometry of the cam surfaces, the force keeping them together, and the optional inclusion of slip springs on the second cam side to provide for oscillation instead of continuous one-directional rotation. The motor, the first cam, and the second cam are disposed in a driver housing, and a wave guide shaft is coupled to the second cam. The wave guide shaft transmits the linear waveform to at least one urinary tract stone to break up the at least one urinary tract stone into fragments.

The invention may be further characterized by one or any of the combinations of the features described herein, such as: a battery that provides electrical energy to the motor is disposed in the driver housing; a controller that provides operating signals to the lithotripter is disposed in the driver housing, the controller providing operating signals for the lithotripter; the lithotripter includes a resistance control to prevent rotation of the second cam; the lithotripter has portions forming an evacuation channel therethough capable of supporting active suction; the wave guide shaft includes a passage extending therethrough so that the passage communicates with the evacuation channel for suctioning of the urinary tract; engagement between the first cam and the second cam converts rotational motion of the first cam to rotational motion of the second cam; the motor and the first cam are an integrated unit; a set of bearings supports the motor within the driver housing; the teeth of the first set of teeth and the teeth of the second set of teeth have a generally triangular shape; the teeth of the first set of teeth and the teeth of the second set of teeth are rounded; the motor is a DC motor; the lithotripter includes a second motor operable to produce a second rotational motion in an opposite direction of the rotational motion produced by the motor; the second rotational motion is converted to rotational motion of the first cam and rotational motion of the second cam when the first cam and the second cam are engaged; and the lithotripter is a disposable single use device.

Accordingly, pursuant to yet another aspect of the invention, there is contemplated a lithotripter that includes a motor operable to produce a rotational motion, a first cam coupled to the motor so that the rotational motion produced by the motor produces rotational motion of the first cam, and a second cam that selectively engages with the first cam so that engagement between the first cam and the second cam converts the rotational motion of the first cam to a linear waveform that is transmitted through the second cam. The motor and the first cam are an integrated unit that is disposed along with the second cam in a driver housing, and a wave guide shaft is coupled to the second cam. The wave guide shaft transmits the linear waveform to at least one urinary tract stone to break up the at least one urinary tract stone into fragments.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses. The present invention relates to a disposable or partially disposable lithotripter for fragmenting stones.

Figure 1:
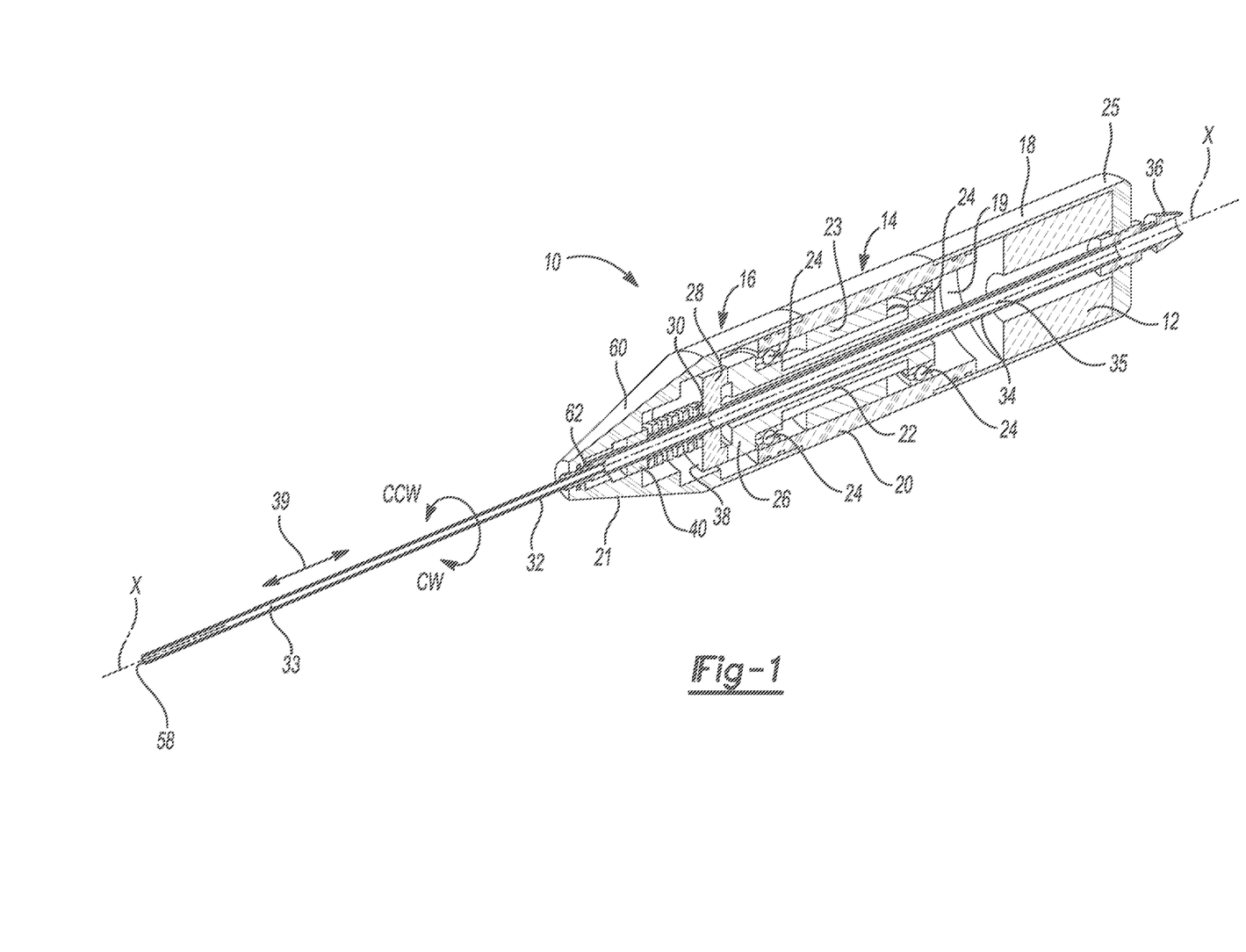
FIG. 1 is a perspective cross-sectional view a lithotripter for fragmenting stones, in accordance with the principles of the present invention.
Figure 2:
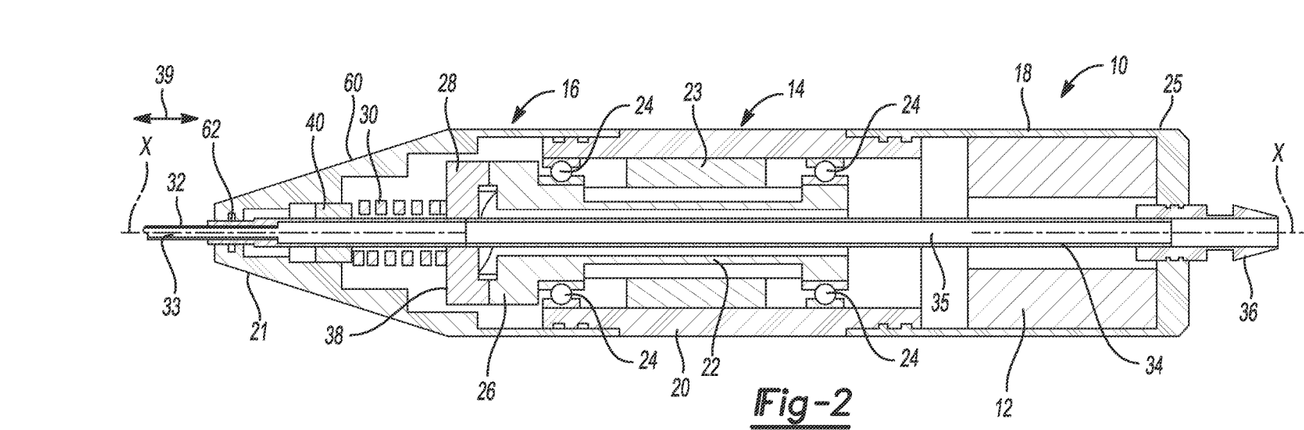
FIG. 2 is a side cross-sectional view of the lithotripter shown in FIG. 1.

With reference to the figures, wherein like numerals indicate like components, and specifically with reference to FIGS. 1 and 2, an example of a lithotripter in accordance with the present disclosure is illustrated and generally designated at 10. The lithotripter may be used for fragmenting stones in a patient's anatomy, such as, for example, in a patient's urinary tract, bladder, or kidneys.

The lithotripter 10 includes a driver housing 18 surrounding a battery and controller unit 12, a motor 14, for example, a DC motor, and a driver 16. The battery and controller unit 12, the motor 14 and the driver 16 are disposed in series within a chamber 19 of the driver housing 18. More specifically, the driver 16 is located towards a distal end 21 of the driver housing 18, the battery and controller unit 12 is located towards a proximal end 25 of the driver housing 18 and the motor 14 is positioned between the driver 16 and the battery and controller unit 12. The battery and controller unit 12 is electrically connected to the motor 14 with, for example, lead wires, and the motor 14 is mechanically coupled to the driver 16.

The motor 14 includes a rotor 22 with one or more magnets. The rotor 22 is disposed within a motor housing 20 and the stator coil 23. Specifically, the rotor 22 is supported within the motor housing 20 with a set of bearings 24, providing the rotor 22 with a rotational degree of freedom about the longitudinal axis, X, extending through the lithotripter 10. As such, when electrical energy from the battery and controller unit 12 is supplied to the stator coil 23, a magnetic field is generated that causes the rotor 22 to rotate within the motor housing 20 and the stator coil 23.

Figure 3:
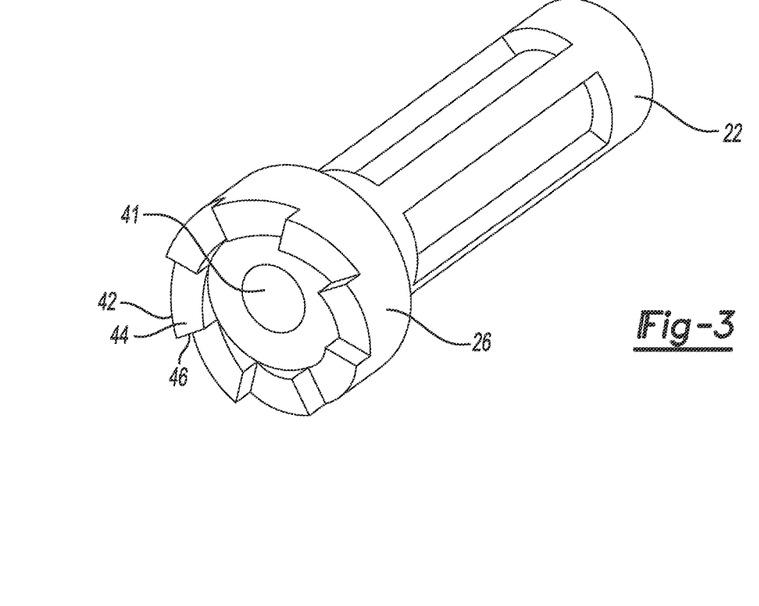
FIG. 3 is a perspective view of a motor rotor integrated with a cam for the lithotripter shown in FIG. 1.
Figure 4:
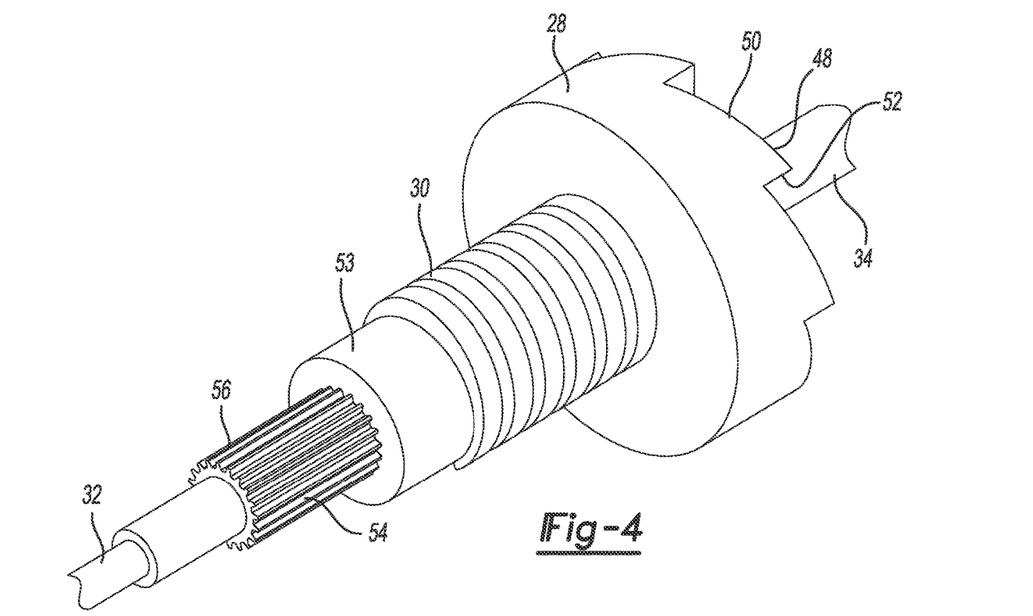
FIG. 4 is a perspective view of another cam that engages with the cam shown in FIG. 3.

The driver 16 includes a first cam 26 that is coupled to the rotor 22 to form an integrated unit. The driver 16 also includes a second cam 28 and a biasing mechanism such as a coiled spring 30. Referring also to FIGS. 3 and 4, the first cam 26 includes a first set of teeth 42, and the second cam 28 includes a second set of teeth 48 that selectively engages with the first set of teeth 42 of the first cam 26. The first set of teeth 42 and the second set of teeth 48 may be formed from a hardened material, such as steel. The coiled spring 30 is positioned between a block 40 and a face 38 of the second cam 28 such that the spring 30 produces a biasing force that urges the second cam 28 against the first cam 26.

Each tooth of the first set of teeth 42 has a slanted surface 44 and a surface 46, and each tooth of the second set of teeth 48 has a slanted surface 50 and a surface 52. Thus, the first set of teeth 42 and the second set of teeth 48 form a set of triangle gears. When the first set of teeth 42 and the second set of teeth 48 are fully engaged, each surface 46 is in contact with a respective surface 52, and each slanted surface 44 is in contact with a respective slanted surface 50.

The second cam 28 of the driver 16 is coupled to a wave guide shaft 32 with a coupler 53. The driver 16 is configured to produce a linear waveform that is transmitted through the wave guide shaft 32 to at least one stone, such as, for example, a urinary tract stone. For example, the wave guide shaft 32 may be partially inserted into the patient through the patient's urethra or percutaneously by way of an incision through the patient's skin. The waveform produced by the driver 16 is delivered to the stone by way of a distal end 58 of the wave guide shaft 32. The wave guide shaft 32 may be rigid, semi-rigid, or flexible.

When the electric motor 14 is energized to rotate the rotor 22 and hence the first cam 26 counterclockwise (ccw, as viewed from the wave guide shaft 32 towards the driver housing 18) about the longitudinal axis, X, the first set of teeth 42 and the second set of teeth 48 are fully engaged. Accordingly, ccw rotation of the first cam 26 causes the second cam 28 as well as the wave guide shaft 32 to rotate ccw. Note that the tube 34 does not rotate about the X axis or translate along the axis.

When the motor 14 is energized to rotate the rotor 22 and the first cam 26 clockwise (cw) about the longitudinal axis, X, the surfaces 46 and 52 separate and the surfaces 50 slide up the surfaces 44 which results in the second set of teeth 48 to separate from the first set of teeth 42. As this occurs, the second cam 28 and the wave guide shaft 32 move linearly away from the first cam 26 and the coiled spring 30 becomes further compressed between the block 40 and the second cam 28. When the first set of teeth 42 and the second set of teeth 48 are at a maximum separation, additional cw rotation of the first cam 26 causes the compressed coiled spring 30 to push the second cam 28 back towards the first cam 26. Therefore, cw rotational motion of the first cam 26 produced by the motor 14 moves the second cam 28 in one direction along the longitudinal axis, X, and the coiled spring 30 moves the second cam 28 in the opposite direction along the longitudinal axis, X. This linear oscillating motion of the second cam 28, as indicated by the double arrow 39, produces a linear waveform that is transmitted through the wave guide shaft 32. Accordingly, when the distal end 58 of the wave guide shaft 33 is placed in contact with a target stone, the linear waveform produces a jackhammer effect on the stone.

The first set of teeth 42 and the second set of teeth 48 may be shaped to maximize the shock delivered to the stone. The coiled spring 30 may include a dampening feature. Note that frictional forces between the first set of teeth 42 and the second set of teeth 48 may cause the second cam 28 as well as the wave guide shaft 32 to rotate cw as the first cam 26 rotates cw. The lithotripter 10 may include a resistance control mechanism 62 that engages, for example, with a gear 54 (FIG. 4) with a set of teeth 56 to prevent rotational motion of the second cam 28 and the wave guide shaft 32.

The lithotripter 10 has portions forming a lumen or channel therethrough for at least one of suctioning and irrigating, for example, a urinary tract. For example, the wave guide shaft 32 has a lumen 33 extending along the length of the wave guide shaft 32. In addition, the lithotripter 10 includes a tube 34 that extends from the distal end 21 through the proximal end 25 of the driver housing 18. More specifically, the tube 34 extends through the second cam 28, the first cam 26, for example, through an opening 41, the rotor 22 and the battery and controller unit 12. The tube 34 has a channel 35 that extends through the tube 34 and communicates with the lumen 33 of the wave guide shaft 32. The tube 34 further includes a connector 36 that provides a mechanism to connect the lithotripter 10 to an irrigation and/or suction tubing for the purposes of irrigating a urinary tract and/or removing waste procedural fluids and stone fragments.

It is contemplated that the frequency and magnitude of the waveform generated by the driver 16 may be selected based on the size of the targeted stone. Hence, the lithotripter 10 may be configured to provide any number of selectable frequencies and magnitudes. In some arrangements, the distal end 58 of the wave guide shaft 32 may be placed in contact with the stone to produce a jack hammer effect on the stone when the lithotripter is activated. In other arrangements, the distal end 58 of the wave guide shaft 32 may be placed adjacent to, but not touching the stone. In some arrangements, the distal end 58 of the wave guide shaft 32 may gently touch the stone, but without a jackhammer effect, such that the oscillation breaks up the stone.

Figure 5:
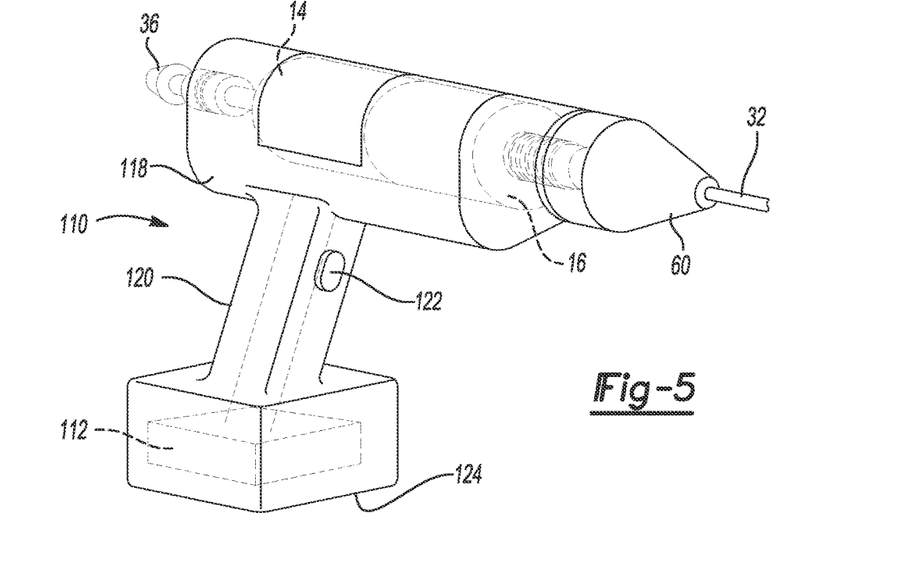
FIG. 5 is a perspective view of another lithotripter for fragmenting stones in accordance with the principles of the present invention.

Referring now to FIG. 5, a variation of a lithotripter in accordance with the principles of the present invention is illustrated and generally designated at 110. The lithotripter 110 includes many of the same components of the lithotripter 10. These components are enclosed in a driver housing 118 and are indicated by like reference numerals. But unlike the lithotripter 10, the lithotripter 110 includes a handle portion 110 connected to the driver housing 118. The lithotripter 110 also includes a compartment 124 that is connected to the handle portion 110. The compartment 124 stores a battery and controller unit 112 that is electrically connected to the motor 14 contained within the driver housing 118. The lithotripter is operated for a particular procedure through the use of a switch 122.

Figure 6:
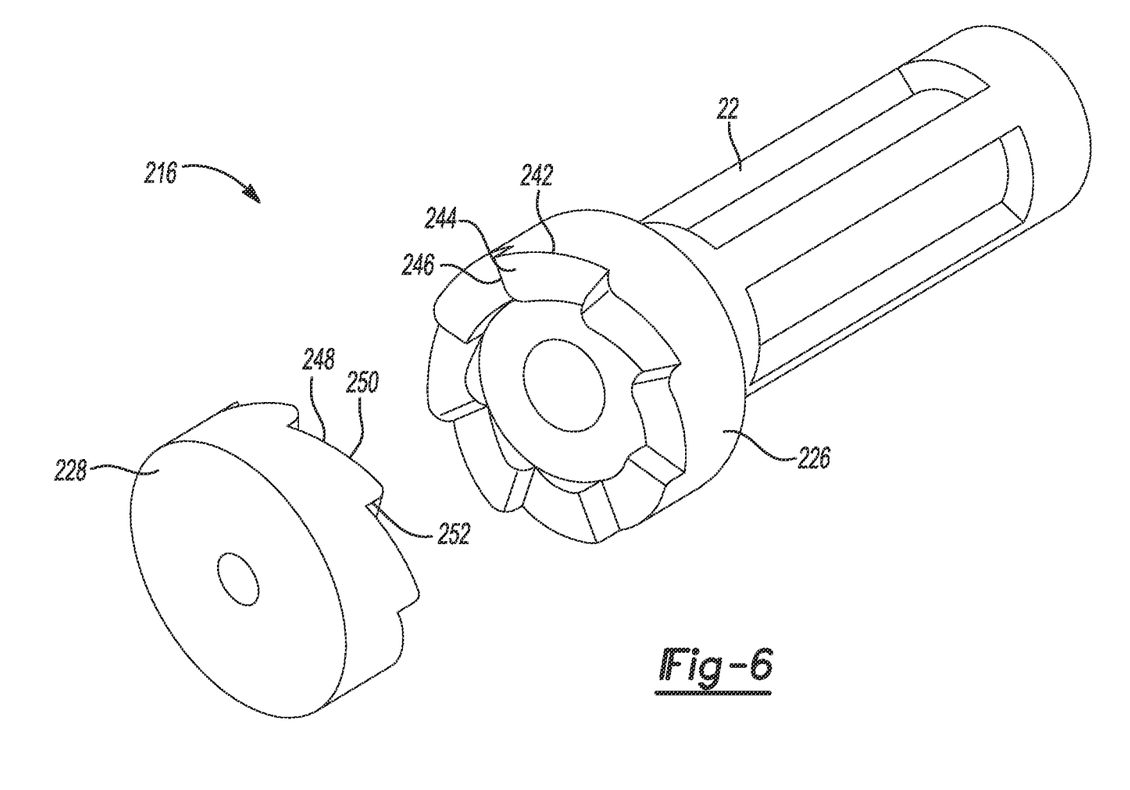
FIG. 6 is a perspective view of another set of cams in accordance with the principles of the present invention.

Referring now to FIG. 6, there is shown an alternative driver 216 with a first cam 226 and a second cam 228. The first cam 226 includes a first set of rounded teeth 242, and the second cam 228 includes a second set of rounded teeth 248 that selectively engages with the first set of teeth 242 of the first cam 226. The first set of teeth 242 and the second set of teeth 248 may be formed from a hardened material, such as steel.

Each tooth of the first set of teeth 242 has a slanted surface 244 and a surface 246, and each tooth of the second set of teeth 248 has a slanted surface 250 and a surface 252. The juncture between the slanted surface 244 and the surface 246 is rounded, and the juncture between the slanted surface 250 and the surface 252 is rounded. When the first set of teeth 242 and the second set of teeth 248 are fully engaged, the surfaces 246 are in contact with respective surfaces 252, and the slanted surfaces 244 are in respective contact with the slanted surfaces 250. The first cam 226 and the second cam 228 can be employed with the lithotripter 10 or the lithotripter 110 in the same way as the first cam 26 and the second cam 28, as described earlier. The shapes of the first set of teeth 242 and the second set of teeth 248 may be formed to maximize the shock delivered to a targeted stone.

Figure 7:
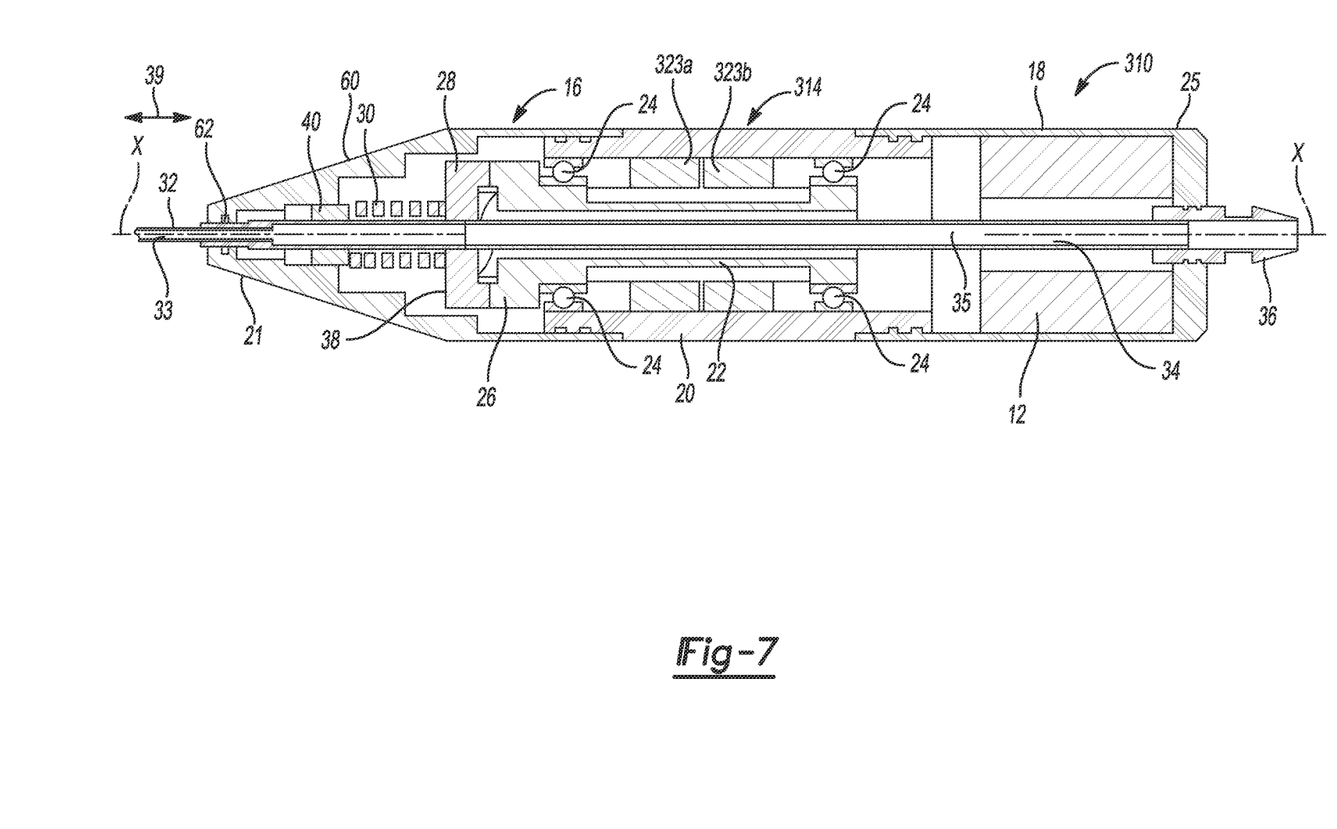
FIG. 7 is a side cross-sectional view of yet another lithotripter for fragmenting stones in accordance with the principles of the present invention.

Turning now to FIG. 7, there is shown a lithotripter 310 in accordance with the principles of the present invention. Lithotripter is similar to the lithotripter 10, but instead of a single motor 14, the lithotripter includes a dual motor 314 with two separate stator coils 323a and 323b. Hence, the dual motor 314 can operate as two separate motors. One motor can be employed to produce rotational motion of the first cam 26 (or 226) in one direction and the other motor employed to produce rotational motion in the opposite direction.

Figure 8:
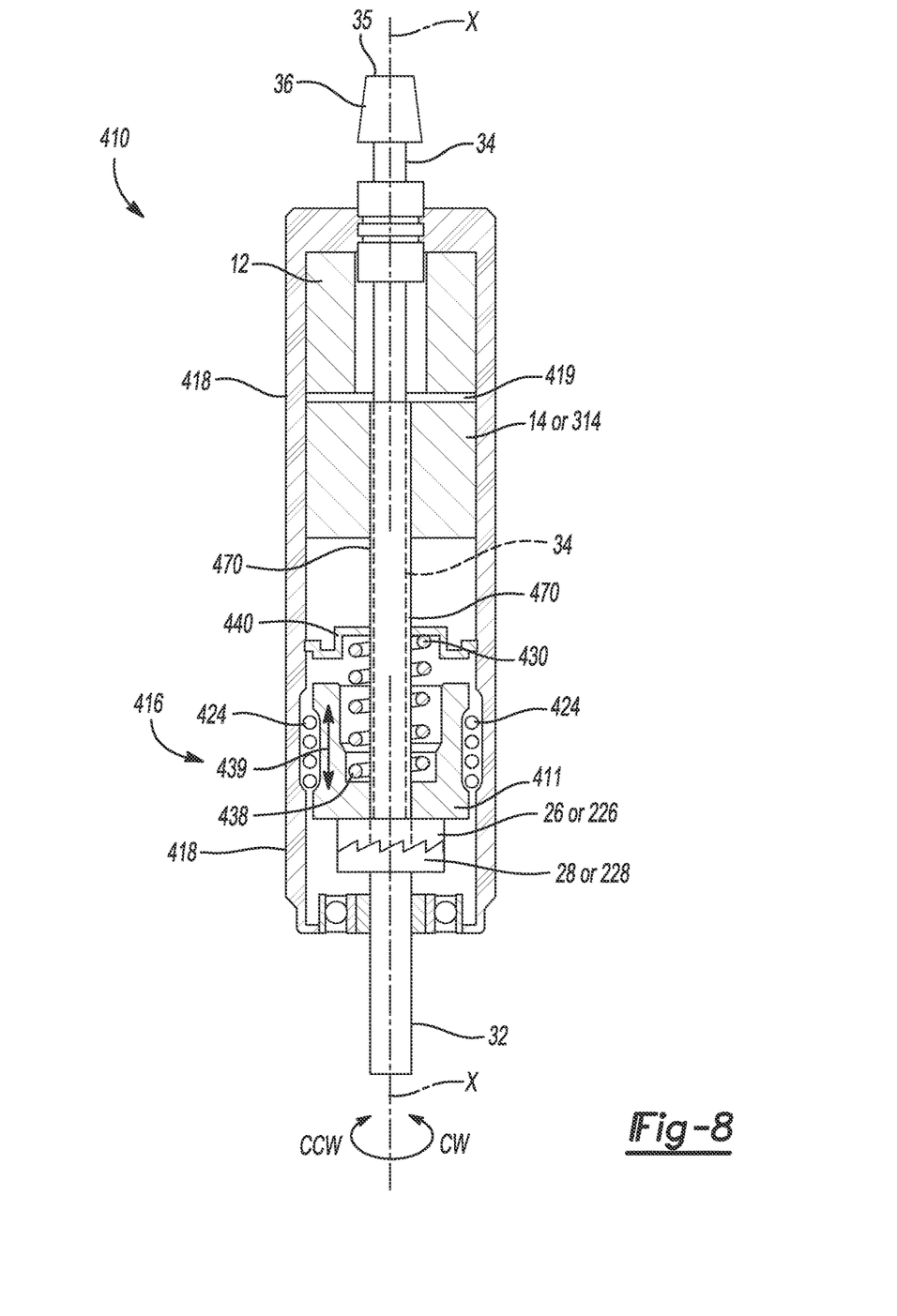
FIG. 8 is a side cross-sectional view of yet another lithotripter for fragmenting stones in accordance with the principles of the present invention.

Referring to FIG. 8, there is shown yet another lithotripter 410 in accordance with the principles of the present invention. The lithotripter 410 includes a driver housing 418 surrounding the battery and controller unit 12, the motors 14 (or 314) and a driver 416. The battery and controller unit 12, the motor 14 (or 314) and the driver 416 are disposed in series within a chamber 419 of the driver housing 418 or arranged similarly to that shown in FIG. 5. The battery and controller unit 12 is electrically connected to the motor 14 (or 314) with, for example, lead wires, and the motor 14 (or 314) is mechanically coupled to the driver 416 with a hollow shaft 470 through which the tube 34 extends.

The driver 416 includes a piston 411 coupled to the shaft 470 and to the first cam 26 (or 226). The piston 411 is supported within the driver housing 418 to provide the piston 411 and the first cam 26 (or 226) both rotational and linear degrees of motion about and along the X axis, respectively. Therefore, when electrical energy from the battery and controller unit 12 is supplied to the motor 14 (or 314), the motor 14 (or 314) rotates the piston 411 together with the first cam 26 (or 226) about the X axis. The driver 416 also includes the second cam 28 (or 228) and a biasing mechanism such as, for example, a coiled spring 430 positioned between a rigid stop 440 and an interior surface 438 of the piston 411. The spring 430 produces a biasing force that urges the first cam 26 (or 226) against the second cam 28 (or 228).

The second cam 28 (or 228) of the driver 416 is coupled to the wave guide shaft 32. Accordingly, the driver 416 is configured to produce a linear waveform that is transmitted through the wave guide shaft 32 to at least one stone, such as a urinary tract stone.

When the electric motor 14 (or 314) is energized to rotate the piston 411 and the first cam 26 (or 226) ccw about the X axis (when looking along the X axis towards the driver housing 418 from the wave guide shaft 32), the first set of teeth 42 (or 242) of the first cam 26 (or 226) and the second set of teeth 48 (or 248) of the second cam 28 (or 228) are fully engaged so that the second cam 28 (or 228) as well as the wave guide shaft 32 rotate ccw.

When the motor 14 (or 314) is energized to rotate the piston 411 and the first cam 26 (or 226) cw about the longitudinal axis, X, the slanted surfaces of the first set of teeth 42 (or 242) of the first cam 26 (or 226) slide up the slanted surfaces of the second set of teeth 48 (or 248) of the second cam 28 (or 228), resulting in the first set of teeth 42 (or 242) separating from the second set of teeth 48 (or 248). As this occurs, the piston 411 and the first cam 26 (or 226) move linearly away from the second cam 28 (or 228) and the coiled spring 430 becomes further compressed between the stop 440 and the piston 411. When the first set of teeth 42 (or 242) and the second set of teeth 48 (or 248) are at a maximum separation, additional cw rotation of the first cam 26 (or 226) causes the compressed coiled spring 430 to push the first cam 26 (or 226) back towards the second cam 28 (or 228), creating an impact force on the bottom portions of the first set of teeth 42 (or 242) and the second set of teeth 48 (or 248). Therefore, cw rotational motion of the first cam 26 produced by the motor 14 (or 314) moves the first cam 26 (or 226) in one direction along the X axis, and the coiled spring 430 moves the first cam 26 (or 226) in the opposite direction, producing a linear oscillating motion of the first cam 26 (or 226), as indicated by the double arrow 439. The impact force between the first cam 26 (or 226) and the second cam 28 (or 228) produces a linear waveform that is transmitted through the wave guide shaft 32 to the target stone. Further note that the lithotripter 410 may be provided with a device similar to the resistance control mechanism 62 and the gear 54 described previously to prevent rotational motion of the wave guide shaft 32.

Any of the aforementioned lithotripters may be single use disposable devices. In other arrangements, certain components of the lithotripter may be disposable, and other components reused. For example, a portion 60 of the lithotripter 10 may be detachable from the remainder of the lithotripter 10 such that the wave guide shaft 32, the spring 30 and the second cam 28 are all disposed of after a single procedure. The other lithotripters described above may have similar disposable components as well.

The description of the invention is merely exemplary in nature and variations that do not depart from the gist of the invention are intended to be within the scope of the invention. Such variations are not to be regarded as a departure from the spirit and scope of the invention.

What is claimed is:

1. A lithotripter for fragmenting urinary tract stones, the lithotripter comprising:
   a motor operable to produce a rotational motion, having an electromagnetic rotor disposed within a stator coil of the motor, the electromagnetic rotor rotating within the stator coil at times electrical energy is supplied to the stator coil;
   a first cam having a first set of teeth, directly coupled to the electromagnetic rotor, forming an integrated unit with the motor;
   a second cam with a second set of teeth configured to selectively engage with the first set of teeth, converting a rotational motion of the first cam generated by the motor to a linear waveform that is transmitted through the second cam;
   a driver housing, wherein the motor, the first cam, and the second cam are disposed in the driver housing;
   a biasing member positioned distally to the second cam between a distal end of the driver housing and the second cam urging the second cam against the first cam; and
   a wave guide shaft coupled to the second cam transmitting the linear waveform to at least one urinary tract stone to break up the at least one urinary tract stone into fragments.

2. The lithotripter of claim 1, further comprising a battery disposed in the driver housing, the battery providing electrical energy to the motor.

3. The lithotripter of claim 2, further comprising a controller disposed in the driver housing, the controller providing operating signals for the lithotripter.

4. The lithotripter of claim 3, further comprising a resistance control to prevent rotation of the second cam.

5. The lithotripter of claim 1, wherein the lithotripter has portions forming an evacuation channel therethough capable of supporting active suction.

6. The lithotripter of claim 5, wherein the wave guide shaft includes a passage extending therethrough, the passage communicating with the evacuation channel for suctioning of the urinary tract.

7. The lithotripter of claim 1, wherein engagement between the first cam and the second cam converts rotational motion of the first cam to rotational motion of the second cam.

8. The lithotripter of claim 1, wherein the motor and the first cam are an integrated unit.

9. The lithotripter of claim 8, further comprising a set of bearings that support the motor within the driver housing.

10. The lithotripter of claim 1, wherein the teeth of the first set of teeth and the teeth of the second set of teeth have a triangular shape.

11. The lithotripter of claim 1, wherein the teeth of the first set of teeth and the teeth of the second set of teeth are rounded.

12. The lithotripter of claim 1, wherein the motor is a DC motor.

13. The lithotripter of claim 1, further comprising a second motor operable to produce a second rotational motion in an opposite direction of the rotational motion produced by the motor.

14. The lithotripter of claim 13, wherein the second rotational motion is converted to rotational motion of the first cam and rotational motion of the second cam when the first cam and the second cam are engaged.

15. The lithotripter of claim 1, wherein the lithotripter is a disposable single use device.

16. A lithotripter for fragmenting urinary tract stones, the lithotripter comprising:
   a motor operable to produce a rotational motion, having an electromagnetic rotor disposed within a stator coil of the motor, the electromagnetic rotor rotating within the stator coil at times electrical energy is supplied to the stator coil;
   a first cam directly coupled to the electromagnetic rotor of the motor, forming an integrated unit with the motor, the rotational motion produced by the motor resulting in rotational motion of the first cam;
   a second cam selectively engages with the first cam, converting the rotational motion of the first cam to a linear waveform that is transmitted through the second cam;
   a driver housing, wherein the motor, the first cam, and the second cam are disposed in the driver housing;
   a biasing member positioned distally to the second cam between a distal end of the driver housing and the second cam, urging the second cam against the first cam; and
   a wave guide shaft coupled to the second cam, transmitting the linear waveform to at least one urinary tract stone to break up the at least one urinary tract stone into fragments.

* * * * *